United States Patent [19]

Weiger et al.

[11] 4,399,705

[45] Aug. 23, 1983

[54] ACCELERATION DETECTOR

[75] Inventors: Günter Weiger, Esslingen; Paul Schwerdt, Freudenstadt; Alfred Ziegenberg, Villingen-Schwenningen, all of Fed. Rep. of Germany

[73] Assignee: Daimler-Benz Aktiengesellschaft, Stuttgart, Fed. Rep. of Germany

[21] Appl. No.: 307,581

[22] Filed: Oct. 1, 1981

[30] Foreign Application Priority Data

Oct. 7, 1980 [DE]  Fed. Rep. of Germany ....... 3037835

[51] Int. Cl.³ .................... G01P 15/08; G01P 15/09; G01L 23/22
[52] U.S. Cl. .................... 73/654; 73/35; 73/517 R; 73/DIG. 4; 310/329
[58] Field of Search ................ 73/35, 654, DIG. 4, 73/517 R; 310/329

[56] References Cited

U.S. PATENT DOCUMENTS 3,307,054  2/1967  Shoor ................... 310/329
3,487,238  12/1969  Angleton et al. ........... 310/329

FOREIGN PATENT DOCUMENTS 547696  2/1977  U.S.S.R. ............ 73/517 R
551565  3/1977  U.S.S.R. ............ 73/517 R

Primary Examiner—E. R. Kazenske
Assistant Examiner—John E. Chapman, Jr.
Attorney, Agent, or Firm—Craig & Burns

[57] ABSTRACT

An acceleration pickup or detector which is provided with a cable outlet located at right angles to a direction of the main vibrations to be detected, especially for detecting knocking signals in internal combustion engines. Connecting elements linking leads of the connecting cable with the acceleration pickup are disposed on a side of the acceleration pickup opposite to the axis of symmetry with respect to the cable outlet. An additional mass is provided on the side of the connecting elements, which mass forms a common counter mass with the connecting elements for the connecting cable.

4 Claims, 4 Drawing Figures

ACCELERATION DETECTOR

The present invention relates to a pickup or detector arrangement and, more particularly, to an arrangement for detecting knocking signals from internal combustion engines, with the pickup or detector being provided with a cable or lead outlet located at right angles to a main vibration direction.

Various methods have been proposed for detecting knocking signals in internal combustion engines, that is, knocking sounds which occur during combustion of excessively lean mixtures or unsuitable fuels. Generally, the principles which govern acceleration measurement along an engine housing impose special requirements on the construction of acceleration pickups or detectors.

In acceleration pickups or detectors wherein a cable or lead outlet is located at one side, it has been found that various resonance points appear in a vicinity of the knocking frequencies, which resonance points have a disturbing effect upon the measurement results obtainable with the pickup or detector.

The aim underlying the present invention essentially resides in providing an acceleration pickup or detector means which is free from interferences affecting the proper functioning of the pickup or detector means so as to permit an undisturbed or a much less disturbed measurement of knocking signals of an internal combustion engine.

In accordance with the present invention, an acceleration pickup or detector is provided with a connecting cable or lead outlet being located at right angles to the main vibration direction to be detected, with the elements connecting the leads of the connecting cable with the acceleration pickup or detector being located on a side of the pickup or detector which is opposite to an axis of symmetry with respect to the cable outlet, and with a further mass being provided on this opposite side. The mass forms a common counter mass to the connecting cable with the connecting elements.

By virtue of the above-noted features of the present invention, a correspondingly designed acceleration pickup or detector results which is largely free of bending moment components thereby making it possible to pickup or detect correspondingly noise-free signals.

Advantageously, in accordance with further features of the present invention, the additional mass is formed by providing a housing or jacket of the acceleration pickup or detector with a thickened portion, which thickened portion is constituted by additional material of the housing or jacket.

Accordingly, it is an object of the present invention to provide an acceleration pickup or detector for detecting knocking signals from an internal combustion engine which avoids, by simple means, shortcomings and disadvantages encountered in the prior art.

Another object of the present invention resides in providing an acceleration pickup or detector for detecting knocking sounds from internal combustion engines which is simple in construction and therefore relatively inexpensive to manufacture.

Yet another object of the present invention resides in providing an acceleration pickup or detector for detecting knocking signals from internal combustion engines which ensures a pickup or detection of the signals in an interference free manner.

A still further object of the present invention resides in providing an acceleration pickup or detector detecting knocking signals from internal combustion engines which functions realiably under all load conditions of the engine.

These and other objects, features, and advantages of the present invention will become more apparent from the following description when taken in connection with the accompanying drawings which show, for the purpose of illustration only, one embodiment in accordance with the present invention, and wherein.

Figure 1:
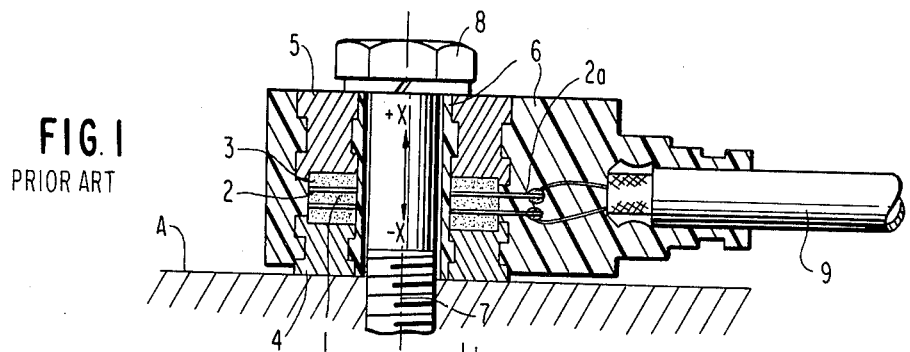
FIG. 1 is a cross sectional view of a previously proposed acceleration pickup or detector.

Referring now to the drawings wherein like reference numerals are used throughout the various views to designate like parts and, more particularly, to FIG. 1, according to this Figure a previously proposed acceleration pickup device includes a piezoceramic element 1 located between two contact strips 2 provided with terminal lugs 2a. The contact strips 2 are both covered by ceramic insulating washers 3 and the stack formed by the contact strips 2 and washers 3 are connected on one side with a metal thrust collar 4 and, on the other side thereof, with a reaction mass 5. Leads of a connecting cable 9 are soldered to the terminal lugs 2a and the entire stack of the element 1, contact strips 2, insulating washers 3, thrust collar 4, and reaction mass 5 are sealed with a jacket 6 made of a sealing or insulating compound, whereby a strain relief is simultaneously formed for the connecting cable 9. A hole, likewise insulated by a sealing or insulating compound, is located in a middle of the stack, with a mounting screw 8 being guided through the hole, which screw 8 is used to draw the acceleration pickup or detector against a surface A of an assembly to be measured. A vibration direction $\pm X$ to be measured is indicated on the shank of the screw 8 by the arrows.

Figure 2:
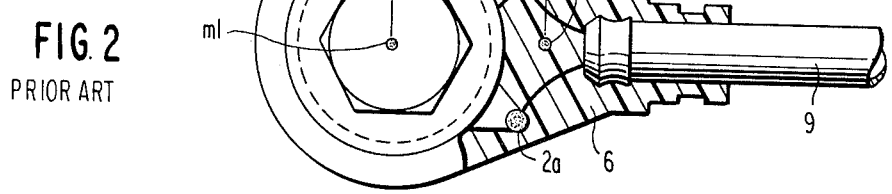
FIG. 2 is a top plan view of the pickup or detector of FIG. 1.

FIG. 2 provides an illustration of the position of the terminal lugs with an axis of symmetry of the stack formed by the element 1, contact strips 2, ceramic insulating washers 3, metal thrust collar 4, and reaction mass 5, being designated by the reference numeral 7. A center of gravity m1 of the acceleration pickup or detector which would lie on the axis of symmetry 7 if it had no terminal lugs 2a or connecting cable 9, is displaced by these latter elements to the point m2; therefore, a lever arm L1 generates bending moment components which have a disturbing effect upon the measurement by the pickup or detector.

Figure 3:
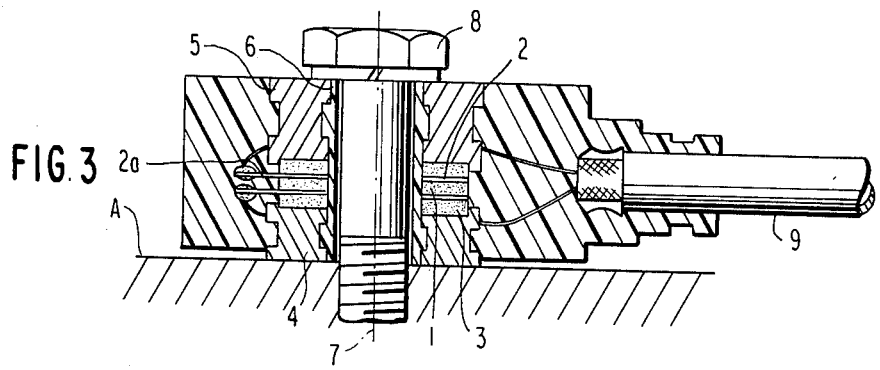
FIG. 3 is a cross sectional view of a pickup or detector constructed in accordance with the present invention.
Figure 4:
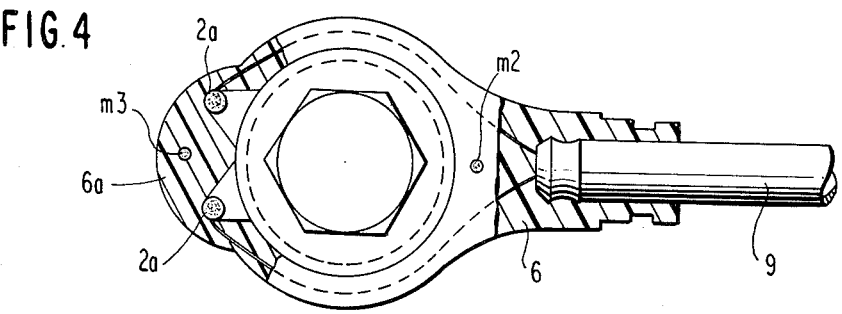
FIG. 4 is a plan view of the acceleration pickup detector of FIG. 3.

To avoid the above-noted disturbing effects, as shown in FIGS. 3 and 4, the terminal lugs 2a of the contact strips 2 are disposed on a side of the pickup or detector which is opposite to the connecting cable 9, relative to the axis of symmetry 7, with a further mass being provided in this area in the form of a thickening of material 6a formed by the material of the housing jacket 6. The further mass forms a countermass m3 with the terminal lugs 2a and the solder applied to the lugs 2a so that the total center of gravity of the pickup or detector is once again located along the axis of symmetry 7 thereby eliminating the occurrence of any disturbing bending moments.

While we have shown and described only one embodiment in accordance with the present invention, it is understood that the same is not limited thereto but is susceptible of numerous changes and modifications as known to one having ordinary skill in the art, and we therefore do not wish to be limited to the details shown and described herein, but intend to cover all such modifications as are encompassed by the scope of the appended claims.

We claim:

1. A detector means for detecting vibrations, the detector means comprising a housing means having a cable outlet means for accommodating connecting leads of a connecting cable means; the cable outlet means being arranged at a right angle with respect to a main direction of vibration to be detected; connecting means are provided for connecting the leads of the cable means with the detector means; said connecting means are disposed on a side of the detector means opposite to the cable outlet means with respect to an axis of symmetry of the detecting means parallel to said direction of vibration; and mass means are provided on the side of the detector means at which the connecting means are disposed for forming with the connecting means a counter mass for the cable means.

2. The detector means according to claim 1, wherein the detecting means is adapted to detect vibrations caused by knocking signals of an internal combustion engine.

3. The detector means according to one of claims 1 or 2, wherein the mass means is formed by a thickening of material of the housing means of the detector means.

4. The detector means according to claim 3, wherein the detector means further includes a piezoceramic element arranged between two contact means; the connecting means includes a connecting lug provided on each of the contact means; insulating washer means are provided for covering the contact means; the piezoceramic element, contact means, and insulating washer means forming a stack of elements disposed in the housing means; and thrust collar means is provided on one side of the stack, and a reaction mass means is provided on the other side of the stack.

* * * * *